US00PP20029P2

(12) United States Plant Patent
Eskelund

(10) Patent No.: US PP20,029 P2
(45) Date of Patent: May 26, 2009

(54) ROSE PLANT NAMED 'EVERA195'

(50) Latin Name: *Rosa hybrida*
Varietal Denomination: Evera195

(75) Inventor: Rosa Eskelund, Fåborg (DK)

(73) Assignee: Roses Flower ApS, Fåborg (DK)

( * ) Notice: Subject to any disclaimer, the term of this patent is extended or adjusted under 35 U.S.C. 154(b) by 0 days.

(21) Appl. No.: 12/154,243

(22) Filed: May 21, 2008

(51) Int. Cl.
*A01H 5/00* (2006.01)

(52) U.S. Cl. ..... Plt./101

(58) Field of Classification Search ..... Plt./101, Plt./102, 109, 116
See application file for complete search history.

*Primary Examiner*—Annette H Para
(74) *Attorney, Agent, or Firm*—C. A. Whealy

(57) ABSTRACT

A new and distinct cultivar of Rose plant named 'Evera195', characterized by its upright and rounded plant habit; dark green-colored leaflets; freely branching growth habit; freely flowering habit; large double red and yellow bi-colored flowers; flowers held upright on strong and erect peduncles; and good postproduction longevity.

3 Drawing Sheets

Botanical designation: *Rosa hybrida.*
Cultivar denomination: 'Evera195'.

BACKGROUND OF THE INVENTION

The present Invention relates to a new and distinct cultivar of Rose plant, botanically known as *Rosa hybrida,* commercially used as a potted Rose, and hereinafter referred to by the name 'Evera195'.

The new Rose is a product of a planned breeding program conducted by the Inventor in Fåborg, Denmark, The objective of the breeding program was to develop new uniform potted Rose varieties with novel and attractive flower colors, disease resistance and excellent postproduction longevity.

The new Rose originated from a cross-pollination made by the Inventor on Mar. 1, 2006 of a proprietary Rose selection identified as code number 05-0206, not patented, as the female, or seed, parent with an unnamed Rose selection, not patented, as the male, or pollen, parent. The new Rose was discovered and selected by the Inventor on May 20, 2006 as a single flowering plant within the progeny of the stated cross-pollination in a controlled greenhouse environment in Fåborg, Denmark.

Asexual reproduction of the new Rose by cuttings in a controlled greenhouse environment at Fåborg, Denmark since Oct. 1, 2006, has shown that the unique features of this new Rose are stable and reproduced true to type in successive generations of asexual reproduction.

SUMMARY OF THE INVENTION

The following traits have been repeatedly observed and are determined to be the unique characteristics of 'Evera195'. These characteristics in combination distinguish 'Evera195' as a new and distinct cultivar of Rose:

1. Upright and rounded plant habit.
2. Dark green-colored leaflets.
3. Freely branching growth habit.
4. Freely flowering habit.
5. Large double red and yellow bi-colored flowers.

6. Flowers held upright on strong and erect peduncles.
7. Good postproduction longevity.

Plants of the new Rose differ from plants of the parent selections in the following characteristics:

1. Plants of the new Rose and the parent selections differ in plant habit as plants of the new Rose are more uniform.
2. Plants of the new Rose and the parent selections differ in flower color as plants of the parent selections have yellow-colored flowers with reddish-colored margins.

Plants of the new Rose can be compared to plants of the Rose 'Evera 117', disclosed in U.S. Plant Pat. No. 17,865. In side-by-side comparisons conducted in Fåborg, Denmark, plants of the new Rose differed from plants of 'Evera 117' in the following characteristics:

1. Plants of the new Rose were more vigorous than plants of 'Evera 117'.
2. Plants of the new Rose had larger flowers than plants of 'Evera 117'.
3. Flowers of plants of the new Rose had more petals than flowers of plants of 'Evera 117'.
4. Plants of the new Rose and 'Evera 117' differed in flower color as plants of 'Evera 117' had dark red-colored flowers.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a side perspective view of a typical plant of 'Evera195' grown in a container.

The photograph on the second sheet of a typical flower of 'Evera195'.

The photograph on the third sheet is a close-up view of the upper surface of a typical leaf, the lower surface of a typical leaf and a typical flower bud (bottom to top).

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown during the winter in Sabro, Denmark, in a glass-covered greenhouse and under commercial production practices. Plants were grown in 12-cm containers, pinched two times and were nine to twelve weeks old when the photographs and description were taken. During the production of the plants, day temperatures averaged 22° C., night temperatures averaged 21° C. and light levels averaged 20,000 lux. In the following description, color references are made to The Royal Horticultural Society Colour Chart, 2001 Edition, except where general terms of ordinary dictionary significance are used.

Botanical classification: *Rosa hybrida* 'Evera195'.

Parentage:

*Female, or seed, parent.*—Proprietary seedling selection of *Rosa hybrida* identified as code number 05-0206, not patented.

*Male, or pollen, parent.*—Unnamed selection of *Rosa hybrida,* not patented.

Propagation:

*Type.*—By cuttings.

*Time to initiate roots.*—About ten to twelve days at 24° C.

*Time to produce a rooted young plant.*—About four weeks at 24° C.

*Root description.*—Fibrous, fine to thick; white in color.

*Rooting habit.*—Freely branching; moderately dense.

Plant description:

*Plant form.*—Upright and rounded plant habit.

*Growth habit.*—Moderately vigorous. Freely branching habit; about three to five lateral branches develop from pinching; dense and bushy growth habit.

*Plant height.*—About 20 cm to 22 cm.

*Plant width* (*spread*).—About 25 cm.

*Lateral branches.*—Length: About 18 cm to 20 cm. Diameter: About 3 mm. Internode length: About 1 cm to 3 cm. Strength: Strong. Texture: Smooth, glabrous. Color: Close to 146C. Thorns: Density: None to about three per linear cm. Shape: Triangular with sharp acuminate apices. Height: About 5 mm to 8 mm. Diameter, at base: About 2 mm to 4 mm. Color, immature: Close to 165C. Color, mature: Close to 175A.

Foliage description:

*Arrangement.*—Alternate; compound with three, five or seven leaflets per leaf.

*Leaf length.*—About 10 cm to 11 cm.

*Leaf width.*—About 7 cm to 8 cm.

*Terminal leaflet length.*—About 5 cm to 6 cm.

*Terminal leaflet width.*—About 3 cm to 3.5 cm.

*Lateral leaflet length.*—About 2.5 cm to 4 cm.

*Lateral leaflet width.*—About 1.5 cm to 2.5 cm.

*Leaflet shape.*—Ovate.

*Leaflet apex.*—Apiculate.

*Leaflet base.*—Truncate to obtuse.

*Leaflet margin.*—Serrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 144A. Developing leaflets, lower surface: Close to 146B. Fully developed, upper surface: Close to 147A; venation, close to 147A. Fully developed, lower surface: Close to 147B tinted slightly with close to 59A; venation, close to 146B to 146C.

*Petioles.*—Leaf petiole length: About 1.5 cm to 2.5 cm. Leaf petiole diameter: About 1 mm. Leaflet petiole length: About 1 mm to 2 mm. Leaflet petiole diameter: About 1 mm. Leaf petiole texture, upper and lower surfaces: Rough. Leaflet petiole texture, upper and lower surfaces: Smooth, glabrous. Leaf petiole color, upper surface: Close to 177A. Leaf petiole color, lower surface: Close to 146B. Leaflet petiole color, upper surface: Close to 177B. Leaflet petiole color, lower surface: Close to 146B.

*Stipules.*—Quantity: Two per leaf. Length: About 5 mm. Width: About 1 mm. Shape: Lanceolate. Apex: Acuminate. Base: Truncate; sessile. Margin: Irregularly serrate to almost entire; ciliate. Texture, upper and lower surfaces: Smooth, glabrous; leathery. Color, upper surface: Close to 137C. Color, lower surface: Close to 146A.

Flower description:

*Flower type and habit.*—Large double flowers with numerous petals. Consistently symmetrical rosette flowers. Flowers borne on erect and strong peduncles; one terminal flower per lateral branch. Flowers persistent.

*Flowering season.*—Year-round under greenhouse conditions, optimal flowering from spring through autumn under garden conditions; flowering intermittent. Plants begin flowering about 78 days after planting.

*Flower diameter.*—About 6 cm.

*Flower depth* (*height*).—About 2 cm.

*Flower longevity on plant.*—About two weeks.

*Fragrance.*—Slightly fragrant; pleasant.

*Flower buds.*—Shape: Ovoid. Length: About 1 cm to 1.5 cm. Diameter: About 7 mm to 9 mm. Color: Close to 143A.

*Petals.*—Quantity: Numerous; about 50 per flower arranged in numerous whorls. Length: About 2 cm to 3 cm. Width: About 1.4 cm to 2.8 cm. Shape: Round to obovate. Apex: Rounded to cuspidate. Base: Attenuate. Margin: Entire. Texture, upper and lower surfaces: Smooth, glabrous. Color: When opening, upper surface: Inner petals: Close to 150C. Outer petals: Close to 150C, shaded with close to 42C. When opening, lower surface: Inner petals: Close to 150B overlain with close to 44C. Outer petals: Close to 42A; towards the base, close to 154B. Fully opened, upper surface: Inner petals: Towards the base, close to 2A; towards the apex, close to 51A. With development, close to 159D. Outer petals: Towards the base, close to 2A; towards the apex, close to 51A. With development, close to 27B speckled with close to 51D. Fully opened, lower surface: Inner petals: Towards the base, close to 3C; towards the apex, close to 27B speckled with close to 51D. Outer petals: Towards the base, close to 154C to 154D; towards the apex, close to 154C to 154D shaded with close to 53A.

*Sepals.*—Quantity per flower: Typically five. Length: About 3 cm to 4 cm. Width: About 5 mm. Shape: Lanceolate. Apex: Sharply pointed. Base: Truncate. Texture, upper and lower surfaces: Pubescent; leathery. Color: When opening, upper surface: Close to 191A to 191B. When opening, lower surface: Darker than 144A. Fully expanded, upper surface: Close to 191A. Fully expanded, lower surface: Close to 137C.

*Peduncles.*—Strength: Strong; flexible. Aspect: Mostly erect. Length: About 2 cm to 2.5 cm. Diameter: About 2 mm to 3 mm. Texture: Smooth, glabrous. Color: Close to 144A.

*Reproductive organs.*—Stamens: Quantity: About 65 per flower. Anther length: About 1 mm to 2 mm. Anther shape: Reniform. Anther color: Close to 165B to 165C. Filament color: Close to 154C to 154D. Pollen amount: None observed. Pistils: Quantity: About 50 per flower. Pistil length: About 1 mm to 2 mm. Stigma color: Close to 144C. Style length: About 1 mm to 2 mm. Style color: Close to 144C. Receptacle shape: Cup-shaped. Receptacle height: About 7 mm. Receptacle diameter: About 7 mm. Receptacle texture: Smooth, glabrous. Receptacle color: Close to 144A. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera195' as illustrated and described.

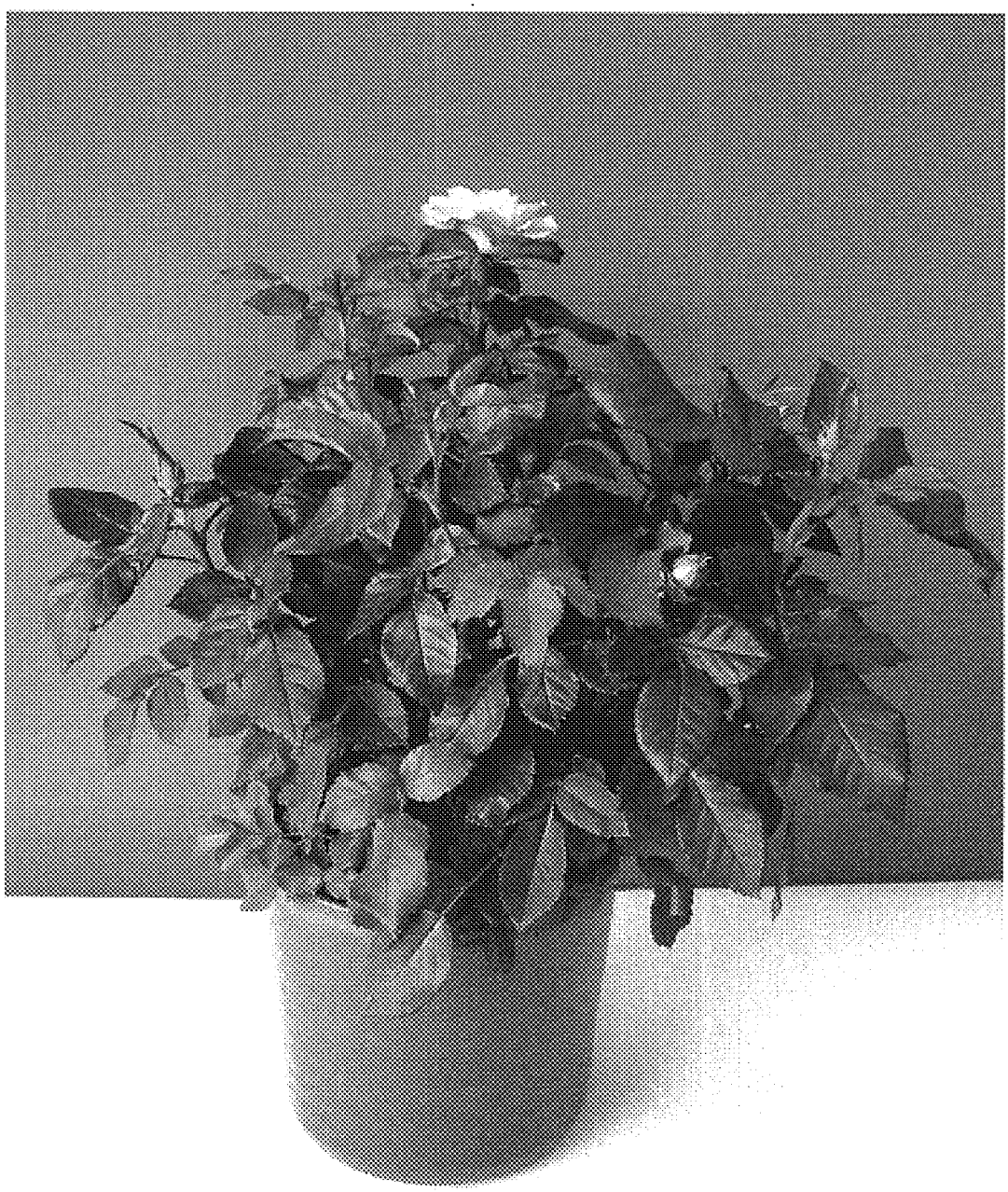

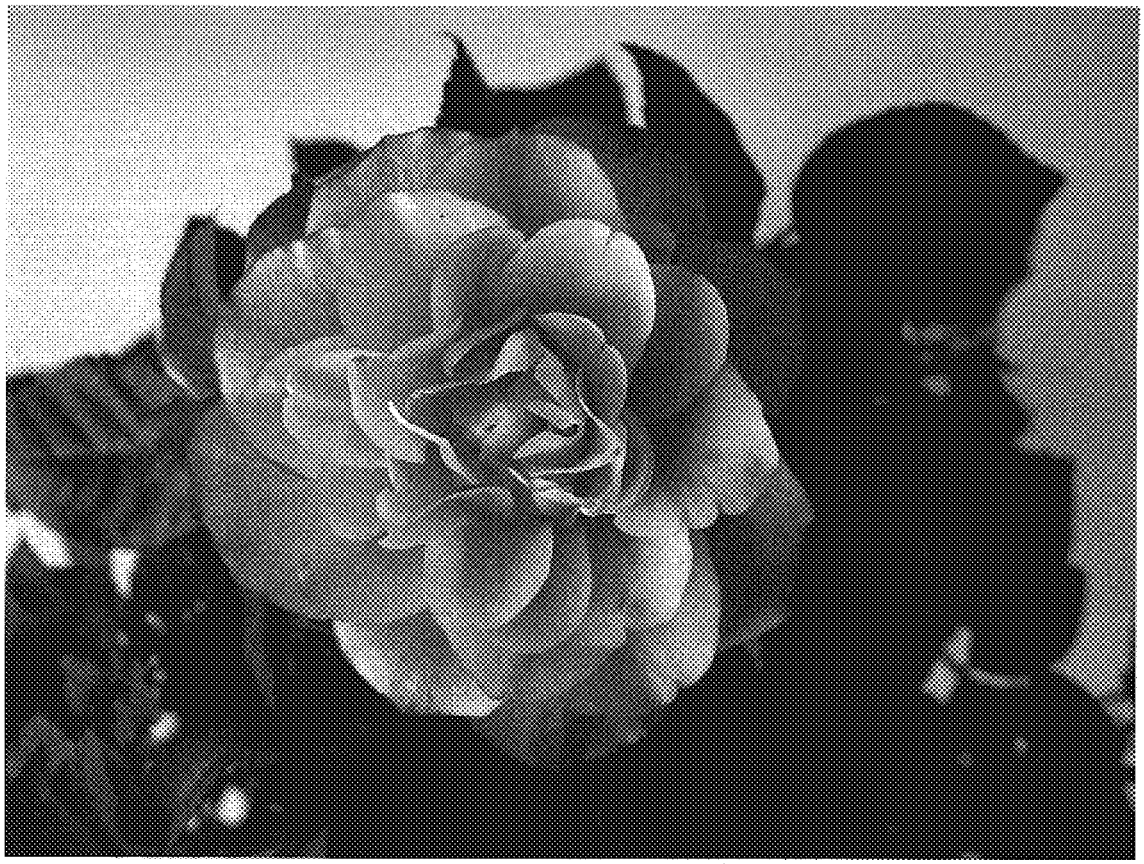

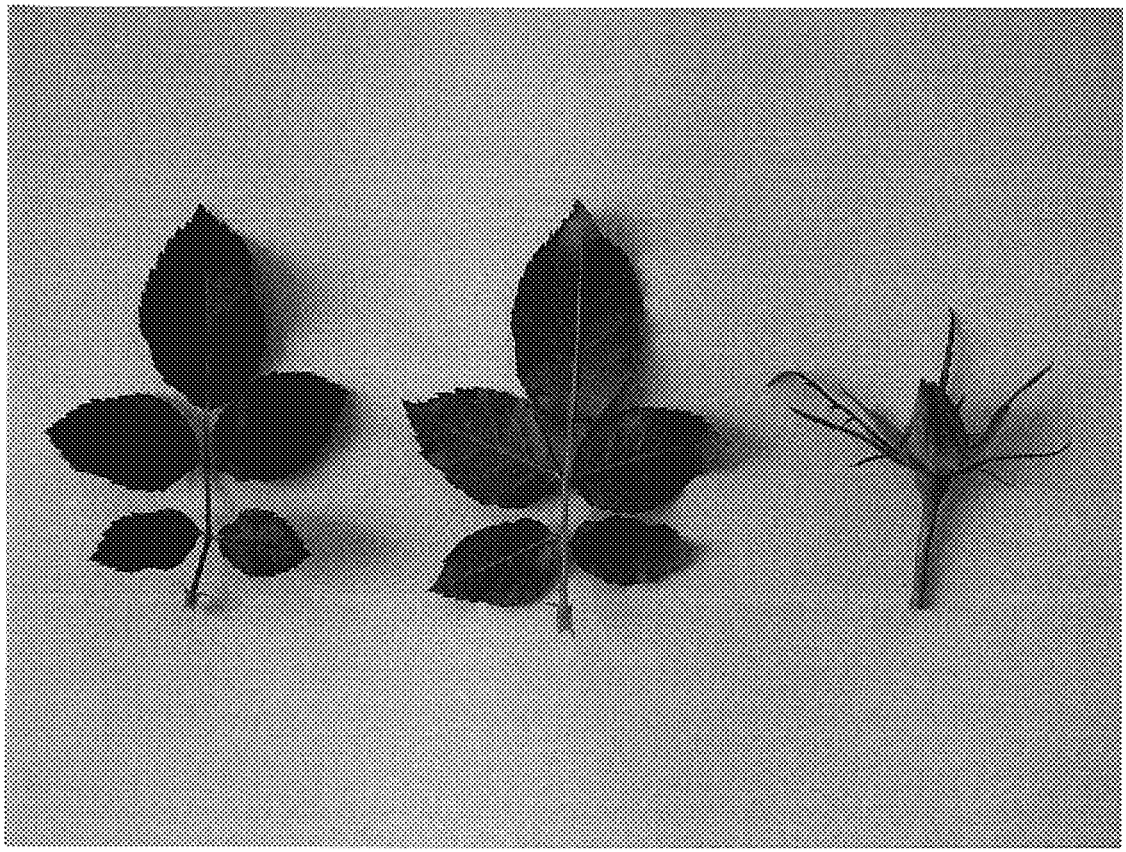

* * * * *